United States Patent
Peguero

(10) Patent No.: US 9,465,914 B2
(45) Date of Patent: Oct. 11, 2016

(54) SYSTEM FOR MONITORING AND RECORDING PATIENT VITAL SIGNS

(71) Applicant: Tara E. Peguero, Salinas, CA (US)

(72) Inventor: Tara E. Peguero, Salinas, CA (US)

( * ) Notice: Subject to any disclaimer, the term of this patent is extended or adjusted under 35 U.S.C. 154(b) by 199 days.

(21) Appl. No.: 14/331,748

(22) Filed: Jul. 15, 2014

(65) Prior Publication Data

US 2016/0019345 A1    Jan. 21, 2016

(51) Int. Cl.
| | |
|---|---|
| *A61B 5/00* | (2006.01) |
| *H04M 11/04* | (2006.01) |
| *G01D 3/08* | (2006.01) |
| *G06F 19/00* | (2011.01) |
| *A61B 5/02* | (2006.01) |
| *A61B 5/046* | (2006.01) |

(52) U.S. Cl.
CPC .......... *G06F 19/322* (2013.01); *A61B 5/0022* (2013.01); *A61B 5/02* (2013.01); *A61B 5/746* (2013.01); *A61B 5/046* (2013.01)

(58) Field of Classification Search
IPC ....................................................... A61B 5/00
See application file for complete search history.

(56) References Cited

U.S. PATENT DOCUMENTS

| | | | | | |
|---|---|---|---|---|---|
| 2002/0099571 | A1* | 7/2002 | Waku | ............... | G06F 19/327 705/2 |
| 2002/0169637 | A1* | 11/2002 | Akers | ............... | G06F 19/322 705/3 |
| 2002/0183976 | A1* | 12/2002 | Pearce | ............... | A61B 5/0006 702/188 |
| 2004/0111014 | A1* | 6/2004 | Hickle | ............... | A61B 5/0002 600/300 |
| 2008/0077026 | A1* | 3/2008 | Banet | ............... | A61B 5/02055 600/509 |
| 2012/0203078 | A1* | 8/2012 | Sze | ............... | G06F 19/3418 600/301 |
| 2014/0067410 | A1* | 3/2014 | Ohta | ............... | G06F 19/3425 705/2 |
| 2014/0288447 | A1* | 9/2014 | Luna | ............... | A61B 5/02438 600/508 |

* cited by examiner

*Primary Examiner* — Jennifer Mehmood
*Assistant Examiner* — Pameshanand Mahase
(74) *Attorney, Agent, or Firm* — McCracken & Gillen LLC

(57) ABSTRACT

A patient vital sign acquisition and recording apparatus for obtaining patient vital sign measurements and recording the vital sign measurements in an electronic medical record is disclosed. A user interface module receives a range of acceptable vital sign measurements and a schedule of how often to record the vital sign measurements. A monitor interface module obtains from a telemetry monitoring system vital sign measurements associated with the patient in accordance with the schedule. An alarm reporting module generates an alarm if the obtained vital sign measurements are outside the range of acceptable vital sign measurements. An interpretation module, in response obtaining the vital sign measurements, causes automatically records the obtained vital sign measurements in an electronic medical record associated with the patient.

7 Claims, 6 Drawing Sheets

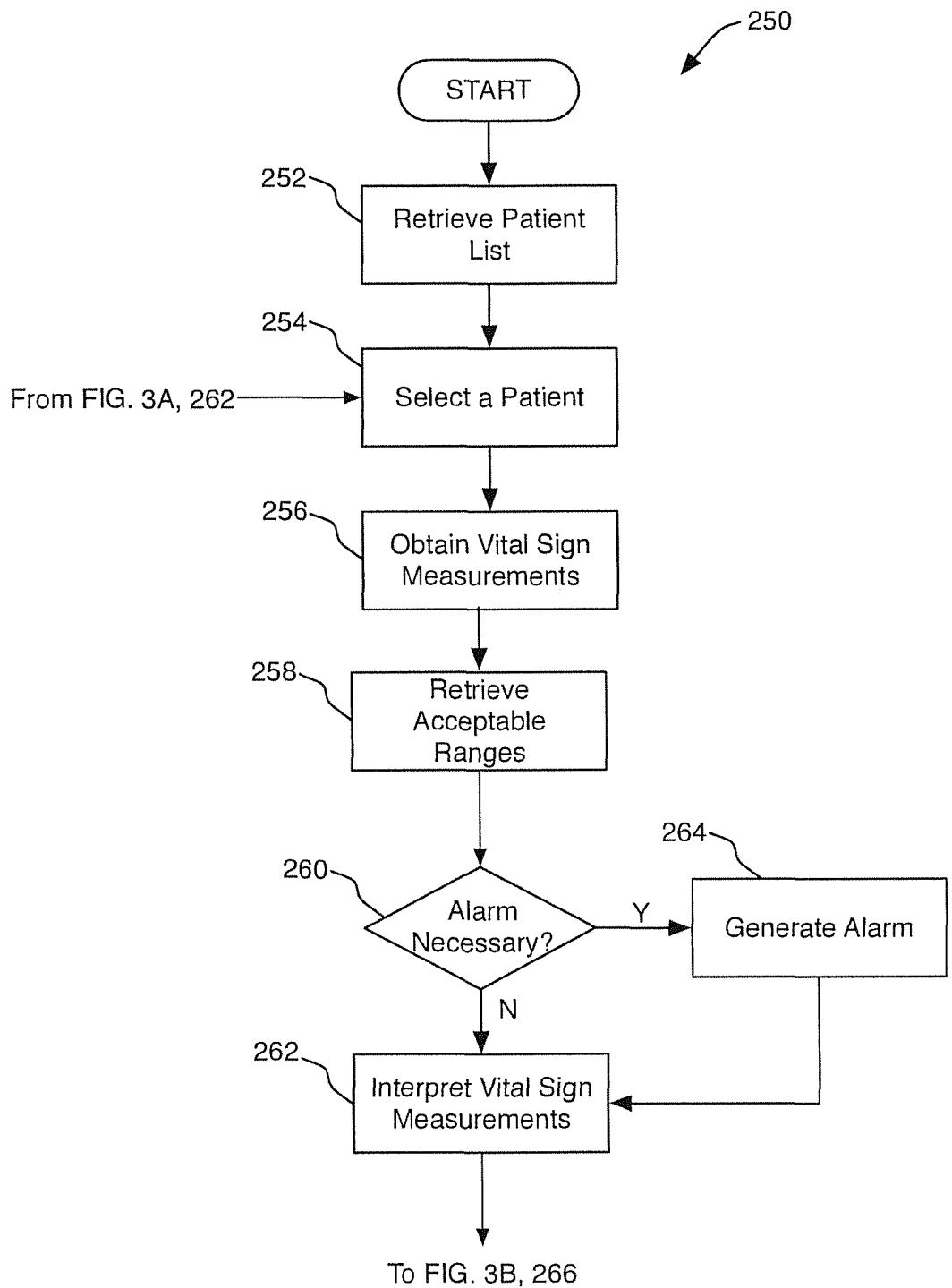

SYSTEM FOR MONITORING AND RECORDING PATIENT VITAL SIGNS

BACKGROUND

1. Field of the Disclosure

The present application is directed to a system for monitoring and recording vital signs of a patient, in particular a system for recording the vital signs of the patient in an electronic medical record associated with the patient.

2. Description of the Background of the Disclosure

When a patient is admitted into a hospital, a medical professional obtains measurements of the vital signs of the patient. Such vital sign measurements may include body temperature, blood pressure, blood oxygen level, heart rate, an electrocardiogram measurement, and the like. Such vital sign measurements are recorded into a medical record associated with the patient. Such electronic record may be a paper-based chart into which the medical professional documents the vital sign measurements. However, such paper-based chart records are being replaced with electronic medial records (EMR) stored in a central computer or server associated with the hospital. The medical professional may use a computer to add the vital signs measurements in the EMR.

A patient telemetry monitoring system may also be used to measure vital signs of the patient. Typically, such a telemetry monitoring system includes sensors secured to the patient that continuously monitor the vital signs thereof. The measurements from the sensors are displayed on a monitor used by the medical professional, for example at a nurse's station or documentation station. Typically, at periodic intervals, a nurse records into a patient's EMR measurements displayed by the telemetry monitoring system. In addition, if one or more vital sign measurements change suddenly, e.g., if a pulse rate changes significantly or an EKG indicates a problematic heart rhythm, the telemetry monitoring system may generate an alarm to notify the nurse of the change in the vital measurements. The nurse thereafter generates a printed record of the vital signs reported by the telemetry monitoring system, and enters the printed record into the medical record associated with the patient if a chart based medical record is being used. If the medical record is an EMR, the nurse may scan the printed record and upload the scan of the printed record into the EMR database. Also, if the telemetry readings need to be sent to a physician for evaluation, the nurse may send the scan, for example, by e-mail, or fax the printed record to the physician.

One nurse in a hospital may be responsible for several patients and have to periodically record vital sign measurements associated with each patient into a medical record of such patient. The periodic recordation of vital sign measurements may be required because of nursing best practices, hospital policy, and/or hospital compliance organizations. Delays in such recordal may occur if there are other more urgent tasks the nurse has to perform. In case of such delay, the nurse may add the vital signs measurements into the medical record associated with a patient when the other tasks are completed. Such a delay may introduce a gap in the vital sign information available to the nurse or the physician attending to the patient.

If an alarm is generated by the telemetry monitoring system with respect to the vital signs measurement of a patient when the nurse is attending to another patient, the vital signs measurement at the time of the alarm may not be available for entry into the EMR associated with the patient.

SUMMARY

According to an aspect of the present disclosure, a computer-implemented system for obtaining patient vital sign measurements and recording the vital sign measurements in an electronic medical record includes a vital sign acquisition and recording apparatus, an electronic interface to a telemetry monitoring system, and an alarm device. A user interface module of the vital sign acquisition and recording apparatus receives a range of acceptable vital sign measurements and a schedule of how often to record the vital sign measurements. A monitor interface module of the vital sign acquisition and recording apparatus automatically obtains from a telemetry monitoring system vital sign measurements associated with the patient in accordance with the schedule. The alarm reporting module of the vital sign acquisition and recording apparatus generates an alarm if the obtained vital sign measurements are outside the range of acceptable vital sign measurements. In response to the vital sign acquisition and recording apparatus obtaining the vital sign measurements, an interpretation module of the vital sign acquisition and recording apparatus automatically records the obtained vital sign measurements in an electronic medical record associated with the patient.

BRIEF DESCRIPTION OF THE DRAWINGS

FIGS. 3A and 3B are flowcharts of execution undertaken by the patient measurement recording system of FIG. 1 to retrieve vital sign measurements, analyze such measurements, and record such measurements in a hospital EMR database;

DETAILED DESCRIPTION

Figure 1:
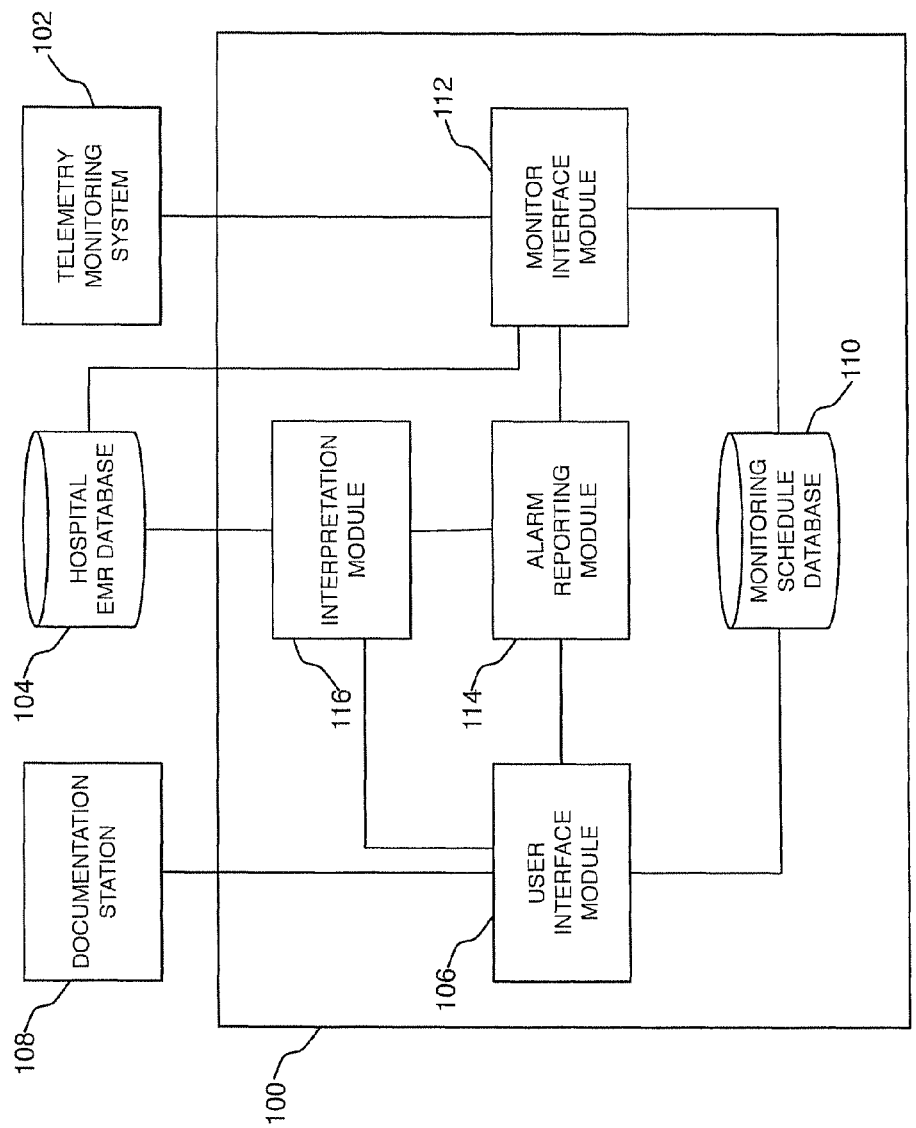
FIG. 1 is a schematic diagram of a patient measurement recording system of the present disclosure.

Referring to FIG. 1, a patient measurement recording system includes a vital sign acquisition and recording apparatus 100 to obtain vital signs measurements associated with one or more patients from a telemetry monitoring system 102 and automatically records such measurements in a hospital EMR database 104.

The vital sign acquisition and recording apparatus 100 includes a user interface module 106 that may display information on a display device at a documentation station 108 and/or receive input from an input device at the documentation system. A nurse or other medical professional may use such display device or input device at the documentation station 108 to interact with the vital sign acquisition and recording apparatus 100 via the user interface module 106. The display device used to display information from the vital sign acquisition and recording apparatus 100 may be used to display vital sign measurements, associated with one or more patients, from one or more telemetry monitoring systems 102. Alternately, the documentation station 108 may include a separate display for displaying information generated by the telemetry monitoring system 102.

The display device and the input device at the documentation station may be coupled directly to the vital sign acquisition and recording apparatus 100. Alternately, such display device and input device may be coupled to a computer that is in communication with the vital sign acquisition and recording apparatus 100. In this case, the user interface module 108 communicates with such computer and directs the computer to display information information on the display device or to receive input from the input device. Although the display device and the input device are described herein as being at the documentation station 108, it should be apparent that such devices may comprise a mobile device that may be used by a nurse or other medical professional to interact with the vital sign acquisition and recording apparatus 100, via the user interface module 106.

A nurse may use the display device and the input device at the documentation station 108 to view and configure monitoring rules for each patient. Such monitoring rules specify how often the vital sign acquisition and recording apparatus 100 should obtain periodic measurements from the telemetry monitoring system 102 and records such schedule in an entry associated with the patient in a monitoring schedule database 110. The monitoring schedule database 110 may include preconfigured monitoring rules and the nurse may use the input device at the documentation station 108 via the user interface module 106 to associate one or more such preconfigured monitoring rules with a patient. In some embodiments, the user interface module 106 may allow the nurse to use the input device at the documentation station 108 to select a plurality of patients and specify a monitoring rule that is common to each of the plurality of patients. In some embodiments, the monitoring schedule database 110 may be preconfigured with default monitoring rules that are applied to all patients. In some cases, the nurse may use input device at the documentation station 108 via the user interface module 106 to modify a pre-configured rule for a particular patient in accordance with the needs of such patient.

In some embodiments, the user interface module 106 may also allow the nurse to view on the display at the documentation station 108 vital sign measurements acquired by the vital sign acquisition and recording apparatus 100.

The user interface module 106 may also allow the nurse to use the input device at the documentation station 108 to specify, for each patient, ranges of vital sign measurements that are acceptable. Such ranges may be specified in accordance with standard ranges known in the art, based on the vital signs measurements taken when the patient was admitted to the hospital, historical ranges associated with a patient (e.g., if patient has been admitted to the hospital multiple times), and the like. Such vital sign range information is also recorded in the entry associated with the patient in the monitoring schedule database 108.

After the monitoring rules and acceptable range information for a patient are stored in the monitoring schedule database, a monitor interface module 112 of the vital sign acquisition and recording apparatus 100 periodically retrieves vital sign measurements from the telemetry monitoring system 102 in accordance with the monitoring rules. Thereafter, the monitor interface module 112 stores the retrieved vital sign measurements into an entry associated with the patient in the hospital EMR database 104.

The monitor interface module 112 may also provide the retrieved vital sign measurements to an alarm reporting module 114 of the vital sign acquisition and recording apparatus 100. The alarm reporting module 114 compares the vital sign measurements of the patient with the acceptable ranges for such vital sign measurements. If the alarm reporting module 114 determines that any of the retrieved vital sign measurements are outside of the acceptable range for such vital sign measurement, the alarm reporting module 114 generates an alarm signal that actuates an alarm device. The alarm device may be an audible alarm generated on a speaker coupled to the vital sign acquisition and recording apparatus 100 and/or a speaker coupled to the documentation station. The alarm device may also be a visual alarm, for example, an illumination device coupled to the vital sign acquisition and recording apparatus 100 and/or an illumination device coupled to the documentation station 108. Other devices and methods that may be used to generate an alarm to notify the nurse will be apparent to those of skill in the art.

In some cases, the monitor interface module 112 may determine that the telemetry monitoring system 112 has generated an alarm. For example, the monitor interface module 112 may detect an indication of such alarm in the retrieved vital sign measurements, or may detect a visual or aural alarm. In such cases, the monitor interface module 112 may automatically retrieve vital sign measurements from the telemetry monitoring system 112 and record such retrieved vital sign measurements in the entry associated with the patient in the EMR database 104. A physician or other medical practitioner may then access such recorded vital sign measurements remotely in response to the alarm generated by the telemetry monitoring system 112.

An interpretation module 116 of the vital sign acquisition and recording apparatus 100 may interpret vital sign measurements and to develop interpreted information and store such information in the entry associated with the patient in the hospital EMR database 104. For example, the interpretation module 116 may analyze the waveform in an electrocardiogram (EKG) strip to determine if the waveform indicates a heart block and, if so, determine the severity (1st degree, 2nd degree, or 3rd degree) of such heart block. The waveform on the EKG strip may also be analyzed to determine if the patient is undergoing ventricular fibrillation or another condition that affects the performance of the heart. In some embodiments, the interpretation module 116 may use the user interface module 106 to display at the documentation station 108, the interpreted information developed thereby. The user interface module 106 may display a prompt on the display device at the documentation station 108 to request the nurse to verify the interpreted information and, if necessary, correct and/or annotate the interpreted information. The nurse may use the input device at the documentation station 108 to provide such verification, correction, and/or annotation. After the nurse has verified the interpreted information, the interpretation module 116 automatically stores the vital sign measurements, a timestamp indicating when the vital sign measurements were acquired, the interpreted information, and any corrections or annotations made by the nurse in an entry associated with the patient in the hospital EMR database 104.

In some embodiments, the interpretation module 116 may analyze a measurement provided by the monitor interface module 112, and measurements and/or interpretation information associated with the patient previously stored in the hospital EMR database 104 to determine how the condition of the patient may be changing over time. The interpretation module 116 also records such interpretation information associated with changes in the condition of the patient in the EMR database 104.

If the interpretation module 116 determines that the patient requires immediate attention, the interpretation module 116 may signal the alarm reporting module 114 to generate an alarm as noted above.

By periodically retrieving and recording patient vital sign measurements, and interpreting such measurements as necessary, the vital sign acquisition and recording apparatus 100 allows a nurse to care for patients who are in need of attention from the nurse. Further, the nurse does not have to periodically stop other tasks to collect and record patient vital sign measurements. The p vital sign acquisition and recording apparatus 100 interrupts the nurse, for example, by generating an alarm, when the vital sign measurements of the patient indicate that attention by the nurse is necessary.

Referring once again to FIG. 1, the user interface module 106, the monitor interface module 112, the alarm reporting module 114, and the interpretation module 116 may be computer-implemented and include a combination of hardware and/or software components. In one example, the vital sign acquisition and recording apparatus 100 may comprise a computer that includes non-transitory, computer-readable memory in which computer-executable instructions may be stored. One or more processors associated with the computer may execute such computer-executable instructions to cause the vital sign acquisition and recording apparatus 100 to undertake the functions of these modules.

The vital sign acquisition and recording apparatus 100 may be implemented on one or more computers. In some embodiments, the modules of the vital sign acquisition and recording apparatus 100 herein may comprise computer executable instructions stored on a non-transitory storage medium, and such instructions may cause one or more processors of the computer(s) to undertake the functions of such modules.

Figure 2:
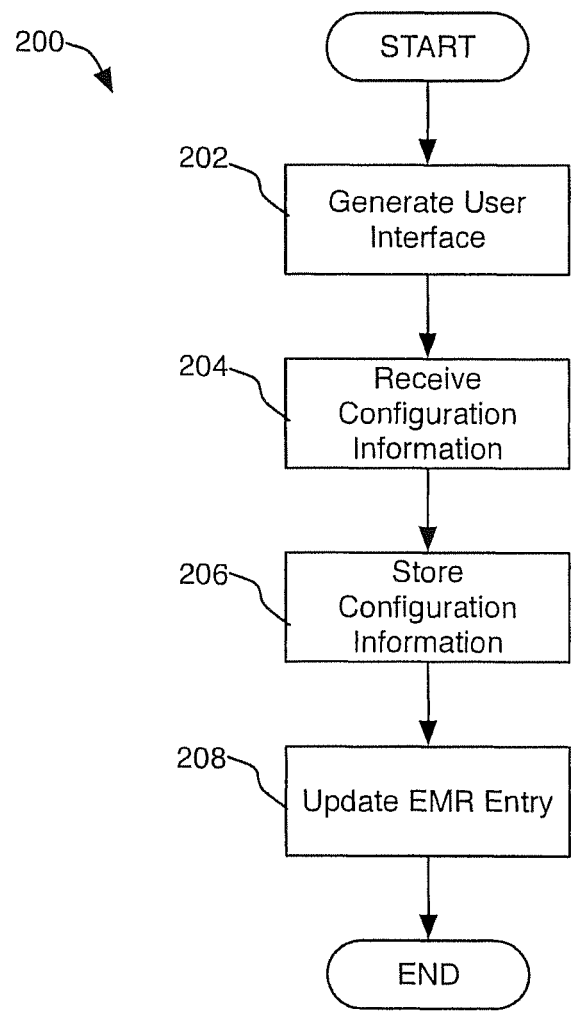
FIG. 2 is a flowchart of execution undertaken by the patient measurement recording system of FIG. 1 to record configuration information associated with a patient.

Referring to FIG. 2, a flowchart 200 shows steps undertaken by the vital sign acquisition and recording apparatus 100 to configure measurement rules and acceptable ranges for a patient. At block 202, the user interface module 106 generates and displays on the documentation station 108 a user interface that a nurse may use to enter configuration information that includes measurement rules that indicates how often vital signs should be recorded and acceptable ranges for such vital signs. The user interface module 106, at block 204, receives the configuration information entered by the nurse at the documentation station 108. At block 206, the user interface module 106 stores the received configuration information in an entry associated with the patient in the monitoring schedule database, at block 204. In some embodiments, the vital sign acquisition and recording apparatus 100 updates an entry in the hospital EMR database 104 associated with the patient to indicate that the configuration information has been received and stored.

Figure 3B:
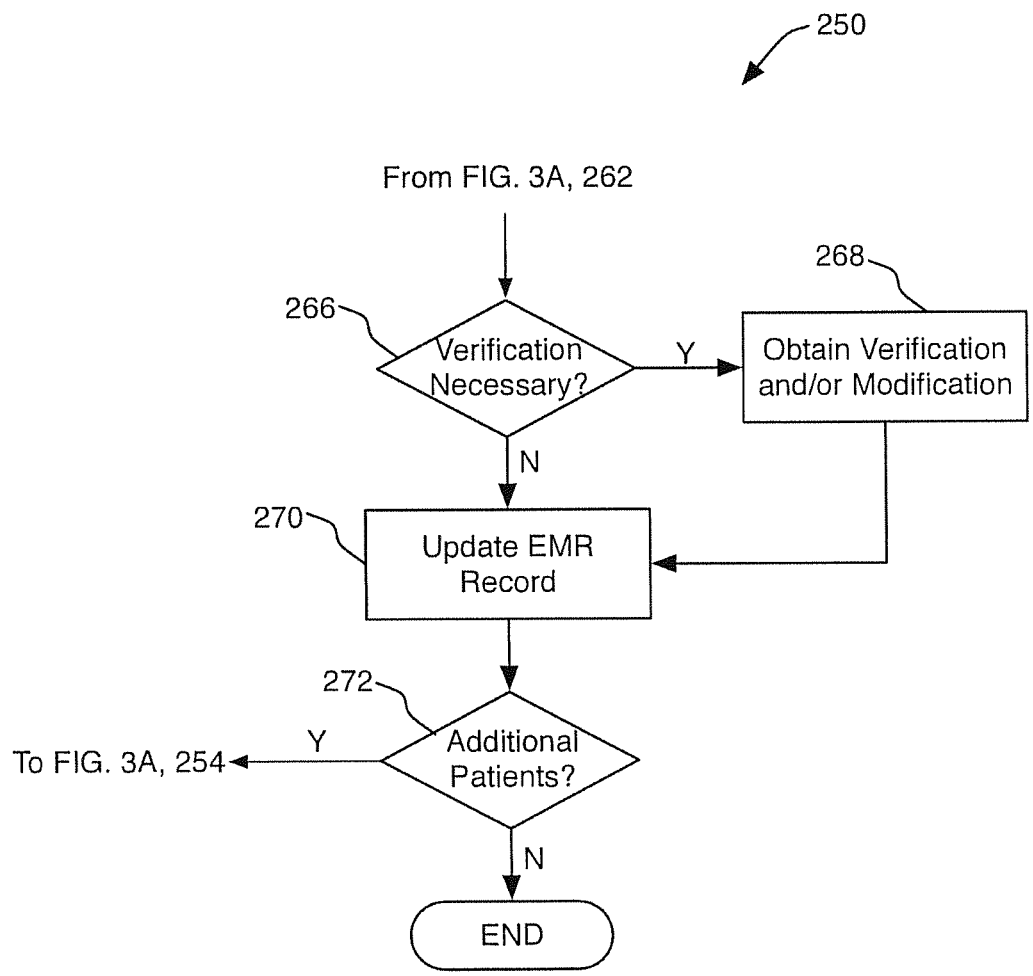

Referring to FIGS. 3A and 3B, a flowchart 250 shows steps undertaken periodically by the vital sign acquisition and recording apparatus 100 to obtain and record vital sign measurements associated with one or more patients. At block 252, the monitor interface module 112 queries the monitoring schedule database 110 for a list of patients whose vital sign measurements should be retrieved and recorded. At block 254, the monitor interface module 112 selects one of the patients from the list of patients.

The monitor interface module 112 retrieves from the telemetry monitoring system 102 vital sign measurements for the selected patient, at block 256. In some embodiments, the monitor interface module 112 may communicate with the telemetry monitoring system 102 using an electronic interface between the vital sign acquisition and recording apparatus 100. In some embodiments such electronic interface includes a network over which the vital sign measurements may be communicated from the telemetry monitoring system 102 to the vital sign acquisition and recording apparatus 100. Such communication may be facilitated, for example, by an application programming interface (API) associated with the telemetry monitoring system 102. In other embodiments, the monitor interface module 112 may use the electronic interface to monitor communications between the telemetry monitoring system 102 and a display associated therewith on which the vital sign measurements are presented. In still other embodiments, the monitor interface module 112 may use the electronic interface to capture an image that represents contents shown on such display, and analyze such image to extract the vital sign measurements. Other ways of obtaining the vital sign measurements from the telemetry monitoring system 102 will be apparent to those who have skill in the art.

At block 258, the alarm reporting module 114 obtains, from the monitoring and schedule database 110, the acceptable ranges for vital sign measurements associated with the selected patient. Then, at block 260, the alarm reporting module 114 compares the vital sign measurements, obtained at block 256, with the acceptable ranges, retrieved at block 258, to determine if any of the obtained measurements are outside of a corresponding range for such measurement. If no measurement is outside the corresponding range, execution proceeds to block 262. Otherwise, the alarm reporting module 114 generates an alarm, at block 264, and execution proceeds to block 262.

At block 262, the interpretation module 116 analyzes the vital sign measurements obtained at block 256 to develop interpreted information. Thereafter, at block 266, FIG. 3B, the interpretation module 116 determines if a nurse needs to verify the interpreted information and, if so, execution proceeds to block 268. Otherwise, execution proceeds to block 270. In some embodiments, the nurse may need to verify the interpreted information if a predetermined amount of time has elapsed since the nurse has verified any acquired information. In other embodiments, the nurse may need to verify the interpreted information if the interpretation module 116 determines that the vital sign measurements obtained at block 256 warrant a nurses attention.

At block 268, the user interface module 106 displays on the documentation station the interpreted information, and obtains from a nurse verification of the interpreted information, any corrections to the interpreted information, and/or any annotations entered by the nurse.

At block 270, the interpretation module 116 updates the entry in the hospital EMR database 104 associated with the patient selected at block 254. In particular, the interpretation module 116 stores in such entry the vital sign measurements obtained at block 256, a timestamp of when such vital sign measurements were obtained, the interpreted information developed at block 262, and any modifications or annotations entered by the nurse at block 266.

At block 272, the monitor interface module 112, checks if vital sign measurements for all of the patients in the list of patients retrieved at block 252 have been retrieved and recorded. If not, execution proceeds to block 254 to select another patient.

In some embodiments, the telemetry monitoring system 102 may generate an alarm condition if a vital sign monitored thereby becomes critical (e.g., if the heart rate or oxygen concentration of a patient drops to a dangerous level). The vital sign acquisition and recording apparatus 100 may monitor the telemetry monitoring system 102 for any such alarms and, in response, retrieve and record vital sign measurements when such alarm is generated.

Figure 4:
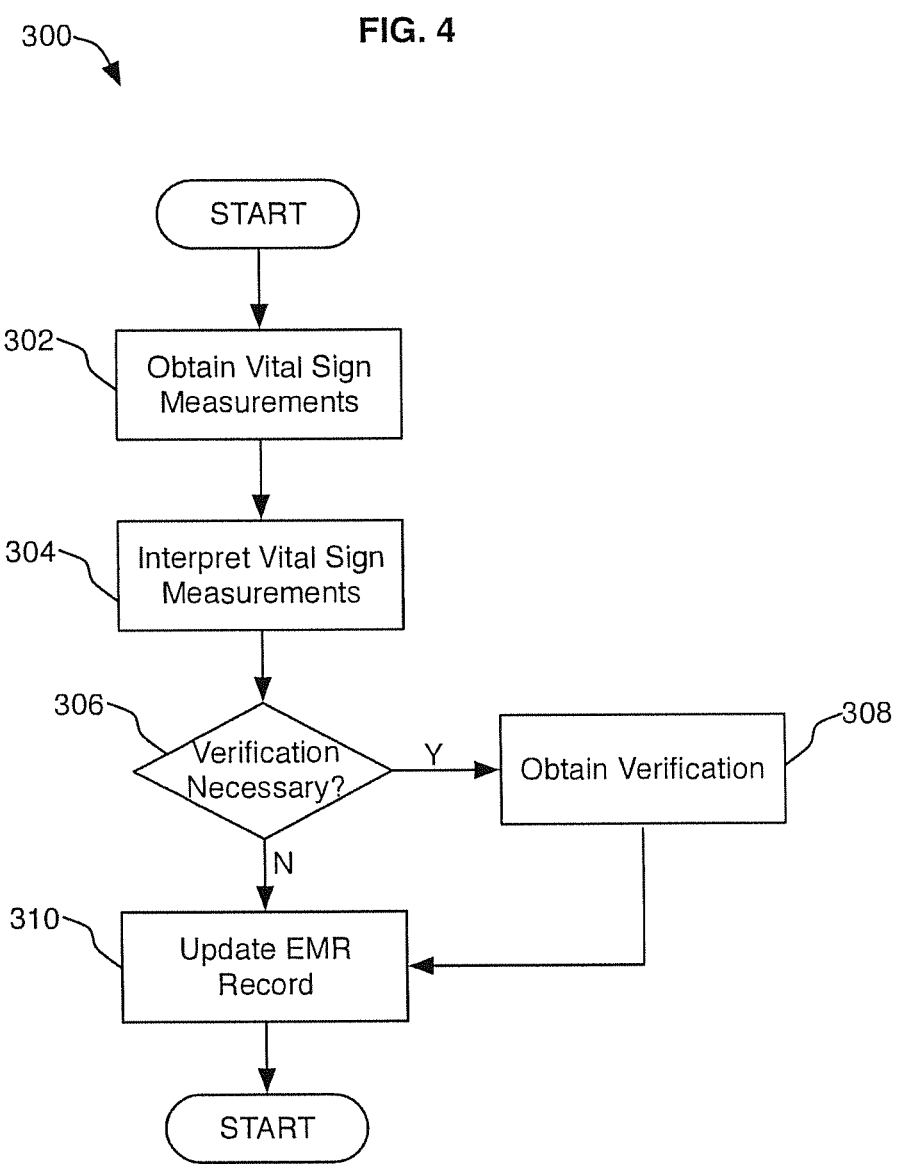
FIG. 4 is a flowchart of execution undertaken by the patient measurement recording system of FIG. 1 in response to an alarm generated by a telemetry system.

Referring to FIG. 4, a flowchart 300 shows the steps undertaken by the vital sign acquisition and recording apparatus 100 in response to an alarm generated by the telemetry monitoring system 102. At block 302, the monitor interface module obtains vital sign measurements from the telemetry monitoring system 102. The interpretation module 116 analyzes the vital sign measurements to develop the interpreted information as described above. At block 306, the interpretation module 116 determines if a nurse or other medical professional needs to verify the interpreted information and, if so, execution proceeds to block 308. Otherwise execution proceeds to block 310.

At block 308, the user interface displays the interpreted information on the documentation station 108, and allows the nurse or other medical professional to verify, modify, and/or annotate such information as described above. Execution then proceeds to block 310.

At block 310, the interpretation module 116 updates the entry in the hospital EMR database 104 of the patient associated with the alarm generated by telemetry monitoring system 102 with the vital sign measurements obtained at block 302, a timestamp of when such vital sign measurements were obtained, the interpreted information developed at block 304, and any modifications or annotations made by the nurse or other medical professional at block 308.

Referring to 5A, and 5B, in one embodiment, the vital sign acquisition and recording apparatus 100 may, at block 260 (FIG. 3A) or at block 300 (FIG. 4), obtain from the telemetry monitoring system 102 vital sign measurements that include, for example, a representation of an EKG 400 (FIG. 5). In some cases, the telemetry monitoring system 102 may provide an image representation of the EKG 400, and the vital sign acquisition and recording apparatus 100 may analyze such image representation to develop a plurality of data points that represent the EKG 400. In other cases, the telemetry monitoring system 102 may provide the plurality of data points that represent the EKG 400. At block 262 (FIG. 3A) or block 304 (FIG. 4), the vital sign acquisition and recording apparatus 100 may analyze the plurality of data points that represent the EKG 400, and determine if the electrocardiogram 400 indicates that the heart rhythm of the patient associated with such electrocardiogram 400 is outside of acceptable ranges. In particular, the vital sign acquisition and recording apparatus 100 may analyze the data points that represent portion 402, 404, 406, 408, 410, and 412 associated with P, Q, R, S, T, and U waves, respectively, that comprise the EKG 400 to determine if the levels of such portions are within acceptable ranges. If the levels of these portions 402, 404, 406, 408, 410, and 412 are within acceptable ranges, at block 270 (FIG. 3B) or block 310 (FIG. 4), the vital sign acquisition and recording apparatus 100 records such levels and, optionally, the EKG 400 in the EMR record associated with the patient.

Figure 5A:
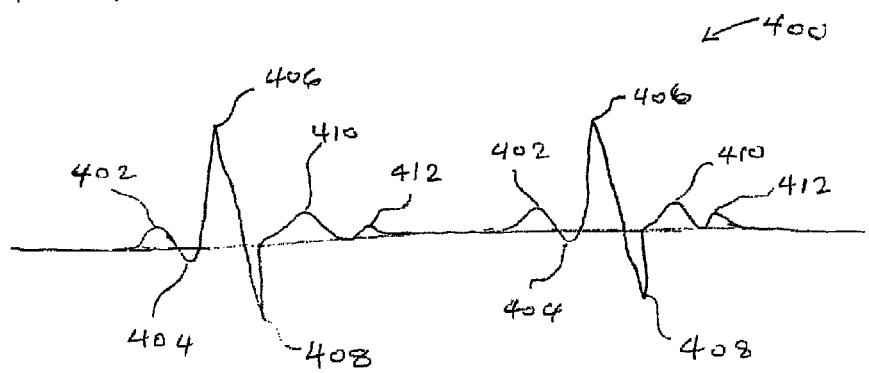
FIGS. 5A, 5B, and 5C are examples of vital sign measurements that may be analyzed by the patient measurement recording system of FIG. 1.

As would be recognized by one of skill in the art, FIG. 5A illustrates an EKG 400 that has portions 402, 404, 406, 408, 410, and 412 that may be considered with acceptable ranges.

Figure 5B:
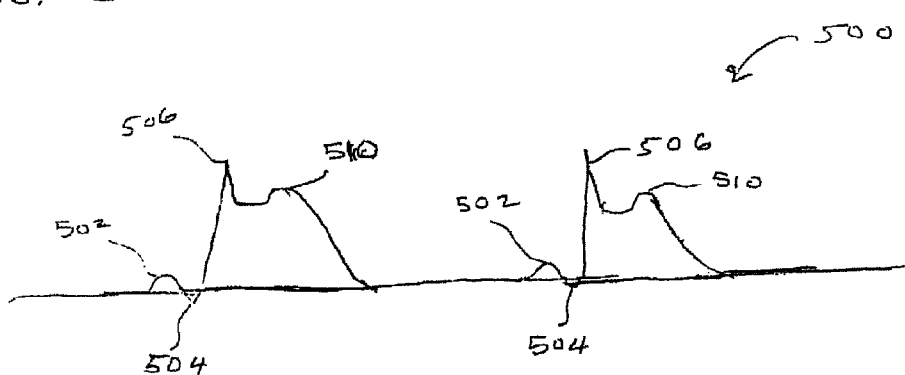
Figure 5C:
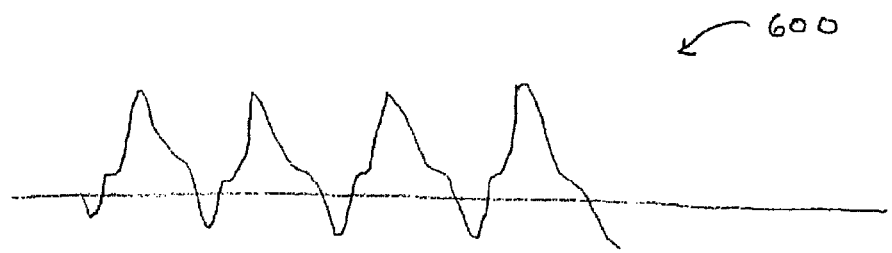

FIG. 5B shows an example of another EKG 500 that has portions 502, 504, 506, and 510 associated with the P, Q, R, and T waves, in which the portion 510 associated with the T wave is elevated compared to the corresponding portion 410 in the normal EKG 400 shown in FIG. 5A. In addition, the EKG 500 does not include any portion that corresponds to the portions 408 and 412 associated with the S and U waves. The vital sign acquisition and recording apparatus 100 may analyze the EKG 500, at block 262 (FIG. 3A) or block 304 (FIG. 4), and determine that such EKG 500 has portions that are outside of the acceptable ranges. In some embodiments, the vital sign acquisition and recording apparatus 100 may further determine that the EKG 500 indicates that the patient is undergoing an ST elevation myocardial infarction. FIG. 5C illustrates yet another EKG 600, which the vital sign acquisition and recording apparatus 100 may analyze and determine that such EKG 600 has a frequency of waves that indicates the patient is undergoing ventricular tachycardia. In such cases, the vital sign acquisition and recording apparatus 100 may request verification and/or annotation of such determination from a nurse or other practitioner, at block 268 (FIG. 3B) or block 308 (FIG. 4), as described above.

Although, FIGS. 5A and 5B show representations of EKGs 400 and 500 that may be analyzed by the vital sign acquisition and recording apparatus 100, EKGs that represent other conditions may be analyzed by the vital sign acquisition and recording apparatus 100 in a manner similar to that described above. Further, it should be apparent to those who have skill in the art that other types of vital sign measurements may be analyzed by the vital sign acquisition and recording apparatus 100 in a similar manner.

It will be understood and appreciated that the vital sign acquisition and recording apparatus may include hardware, software, or a combination of hardware and software on one or more electronic or digitally-controlled devices. The software may reside in a software memory in a suitable electronic processing component or system such as, for example, one or more of the functional systems, controllers, devices, components, modules, or sub-modules. The software memory may include an ordered listing of executable instructions for implementing logical functions (that is, "logic" that may be implemented in digital form such as digital circuitry or source code, or in analog form such as analog source such as an analog electrical, sound, or video signal). The vital sign acquisition and recording apparatus may include, for example, one or more microprocessors, general purpose processors, combinations of processors, digital signal processors (DSPs), field programmable gate arrays (FPGAs), or application-specific integrated circuits (ASICs). The example systems described in this application may be implemented in a variety of configurations and operate as hardware/software components in a single hardware/software unit, or in separate hardware/software units.

As described herein, the vital sign acquisition and recording apparatus 100 may include a computer and a computer program product having instructions stored in a non-transitory computer-readable storage medium associated therewith and which, when executed by a processing module of an electronic system, direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical).

It will also be understood that receiving and transmitting of data as used in this document means that two or more systems, engines, databases, devices, components, modules, or sub-modules are capable of communicating with each other via signals that travel over some type of signal path. The signals may be communication, power, data, or energy signals, which may communicate information, power, or energy from a first system, engine, database, device, component, module, or sub-module to a second system, engine, database, device, component, module, or sub-module along a signal path between the first and second system, engine, database, device, component, module, or sub-module. The signal paths may include physical, electrical, magnetic, electromagnetic, electrochemical, optical, wired, or wireless connections. The signal paths may also include additional systems, engines, databases, devices, components, modules, or sub-modules between the first and second system, device, component, module, or sub-module.

INDUSTRIAL APPLICABILITY

Numerous modifications to the embodiments disclosed herein will be apparent to those skilled in the art in view of the foregoing description. Accordingly, this description is to be construed as illustrative only and is presented for the purpose of enabling those skilled in the art to make and use the disclosed embodiments and to teach the best mode of carrying out same. The exclusive rights to all modifications that come within the scope of the disclosed embodiments are reserved.

What is claimed is:

1. A patient vital sign recording system for obtaining patient vital sign measurements and recording the vital sign measurements in an electronic medical record, the system comprises:
    a vital sign acquisition and recording apparatus;
    an electronic interface to a telemetry monitoring system;
    an alarm device, wherein the alarm device includes a visual or aural indicator;
    a user interface module of the vital sign acquisition and recording apparatus that receives a range of acceptable vital sign measurements and a schedule of how often to record the vital sign measurements;
    a monitor interface module of the vital sign acquisition and recording apparatus that automatically obtains via the electronic interface from the telemetry monitoring system vital sign measurements associated with a patient in accordance with the schedule;
    an alarm reporting module of the vital sign acquisition and recording apparatus that determines if the obtained vital sign measurements are outside the range of acceptable vital measurements, and if so, the vital sign acquisition and recording apparatus actuates the alarm apparatus; and
    an interpretation module of the vital sign acquisition and recording apparatus that, in response to the vital sign acquisition and recording apparatus obtaining the vital sign measurements, interprets the obtained vital sign measurements to develop interpreted information; and
    wherein the user interface module displays on a screen in communication therewith the interpreted information and receives from a first user one or both of a correction to the interpreted information and an annotation to the interpreted information, and the interpretation module records the interpreted information, any correction to the interpreted information and any annotation to the interpreted information in an electronic medical record associated with the patient, and the information recorded by the interpretation module is provided to a second user.

2. The system of claim 1, wherein the vital sign measurements include an electrocardiogram waveform.

3. The system of claim 2, wherein the interpreted information includes an assessment that the electrocardiogram waveform indicates a heart block and a severity of the heart block.

4. The system of claim 2, wherein the interpreted information includes an assessment that the electrocardiogram waveform indicates ventricular fibrillation.

5. The system of claim 1, wherein the monitor interface module determines that the telemetry monitoring system has generated an alarm and, in response to the generated alarm, retrieves vital sign measurements from telemetry monitoring system; and
    the interpretation module stores the retrieved measurements in the electronic medical record associated with the patient.

6. The system of claim 1, wherein an image of vital sign measurements displayed on a monitor associated with the telemetry monitoring system is obtained by the vital sign acquisition and interpretation apparatus, and the monitor interface module analyzes the image to extract the vital sign measurements.

7. The system of claim 1, wherein the monitor interface module monitors data sent by the telemetry monitoring system to a display associated with the telemetry monitoring system, and the monitor interface module extracts the vital sign measurements from the data.

* * * * *